United States Patent [19]

Warriner

[11] Plant 4,813

[45] Jan. 26, 1982

[54] ROSE PLANT 72-14691

[75] Inventor: William A. Warriner, Tustin, Calif.

[73] Assignee: Jackson & Perkins Company, Medford, Oreg.

[21] Appl. No.: 189,570

[22] Filed: Sep. 23, 1980

[51] Int. Cl. ..... A01H 5/00

[52] U.S. Cl. ..... Plt./14

[58] Field of Search ..... Plt./14

*Primary Examiner*—James R. Feyrer

*Attorney, Agent, or Firm*—Klarquist, Sparkman, Campbell, Leigh, Whinston & Dellett

[57] ABSTRACT

A hybrid tea rose variety having non-fragrant, double white blooms on a vigorous, slightly angular growing bush.

1 Drawing Figure

1

This present invention relates to a new and distinct variety of rose plant of the hybrid tea class, which was originated by me by crossing the variety Tonight, U.S. Plant Pat. 3,522, with pollen of the variety Coral Satin, U.S. Plant Pat. No. 2,098.

The purpose of this type of breeding, a red hybrid tea with pollen of a coral pink climbing variety, was exploratory in that no prediction could be made as to the type of progeny expected. This particular selection from the seedlings of this cross is a bush type hybrid tea bearing white flowers.

This variety is new and unique as evidenced by the following combination of characteristics which are outstanding and which distinguish it from its parents as well as from all other varieties of which I am aware:

1. A vigorous, well branched, slightly angular habit of growth.
2. Reddish purple new foliage.
3. Nearly white buds, tinted slightly, especially near the petal tips, with pink.
4. A fully double, over 40 petals, open flower of near white.
5. Open flower form is such that outer petals are positioned straight out (90°) from the stem axis; and center petals cover the reproductive parts of the flower.
6. Little or no fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in color illustrations of this character.

The following is a detailed description of my new rose cultivar with color in terminology in accordance with the Royal Horticultural Society Colour Chart except where ordinary dictionary significance of color is indicated.

Parentage:

*Seed parent.*—Tonight, U.S. Plant Pat. No. 3,522.

*Pollen parent.*—Coral Satin, U.S. Plant Pat. No. 2,098.

Classification:

*Botanical.*—Rosa hybrid.

*Commercial.*—Hybrid tea.

2

FLOWER

Observations made from specimens grown at Irvine, Calif., In August, 1980.

Blooming Habit: Continuous.

Bud:

*Size.*—1½" when petals start to unfurl.

*Form.*—Short, pointed ovoid.

*Color.*—When sepals first divide, nearly white with a pale tinting of pink, Group 56D near petal edges. When half blown, upper side of petals near white, but when viewed from straight above appears to be near Yellow-Orange 18C; lower side of petals, white.

*Sepals.*—Color: outer surface, Green 144B. Surface has numerous stipitate glands. Three appendaged sepals lightly appendaged; two unappendaged sepals hairy edged.

*Receptacle.*—Color: Green 144B. Shape: funnel. Size: large, broad. Surface: smooth.

*Peduncle.*—Length: medium. Surface: prickly. Color: light green. Strength: stiff, erect.

Bloom:

*Size.*—Large. Average open size is 5 inches.

*Borne.*—Singly or several together.

*Stems.*—Long to medium.

*Form.*—When first open, high centered. Permanence: all petals curl, slightly quill fashion.

*Petalage.*—Number of petals under normal conditions, 40 plus.

*Color.*—Center of flower: upper side of petals, white; reverse side of petals, white; base of petals, light yellow, near 7D. General tonality from a distance, white.

*Variegations.*—Occasional spotting from weather.

*Discoloration.*—General tonality at end of first day, white. At third day, white.

*Fragrance.*—None.

Petals:

*Texture.*—Thin, strong substance.

*Shape.*—Round.

*Form.*—Edges slightly quilled.

*Arrangement.*—Irregular. Petaloids in center, few.

*Persistence.*—Drop off cleanly.

*Lastingness.*—On the plant, long. As cut flower, long.

Reproductive parts:

*Anthers.*—Medium. Color: yellow. Arrangement: regular around styles, and mixed with petaloids.
*Filaments.*—Color: yellow, white when old.
*Pollen.*—Lemon yellow.
*Styles.*—Color: very light rose pink.
*Stigmas.*—Color: white.

PLANT

Form: Bush.
Growth: Very vigorous, branching.
Foliage: Number of leaflets on normal mid-stem leaves, 5 or 7.
*Size.*—Large.
*Quantity.*—Normal.
*Color.*—New foliage: Purple 59A. Old foliage: Green 139A.
Leaflets:
*Shape.*—Broad, oval.
*Texture.*—Upper side, leathery.
*Edge.*—Serrated.
*Serration.*—Single, small.
*Petiole.*—Rachis: color: green. Underside: prickles.
*Stipules.*—Long, bearded.

*Disease resistance.*—Normally resistant to mildew under normal growing conditions at Irvine, Calif.
Wood:
*New wood.*—Color: light green. Bark: smooth.
*Old wood.*—Color: green. Bark: smooth.
Prickles:
*Quantity.*—On main stalks from base, ordinary. On laterals from stalk, ordinary.
*Form.*—Long base, medium, straight.
*Color when young.*—Brown.
*Position.*—Irregular.
Small prickles:
*Quantity.*—On main stalks, few. On laterals, few.
*Color.*—Brown.

I claim:

1. A new and distinct variety of rose plant of the hybrid tea class, substantially as herein shown and described, characterized particularly as to novelty by the unique combination of its vigorous, slightly angular plant habit, near white buds opening into non-fragrant, double white blooms.

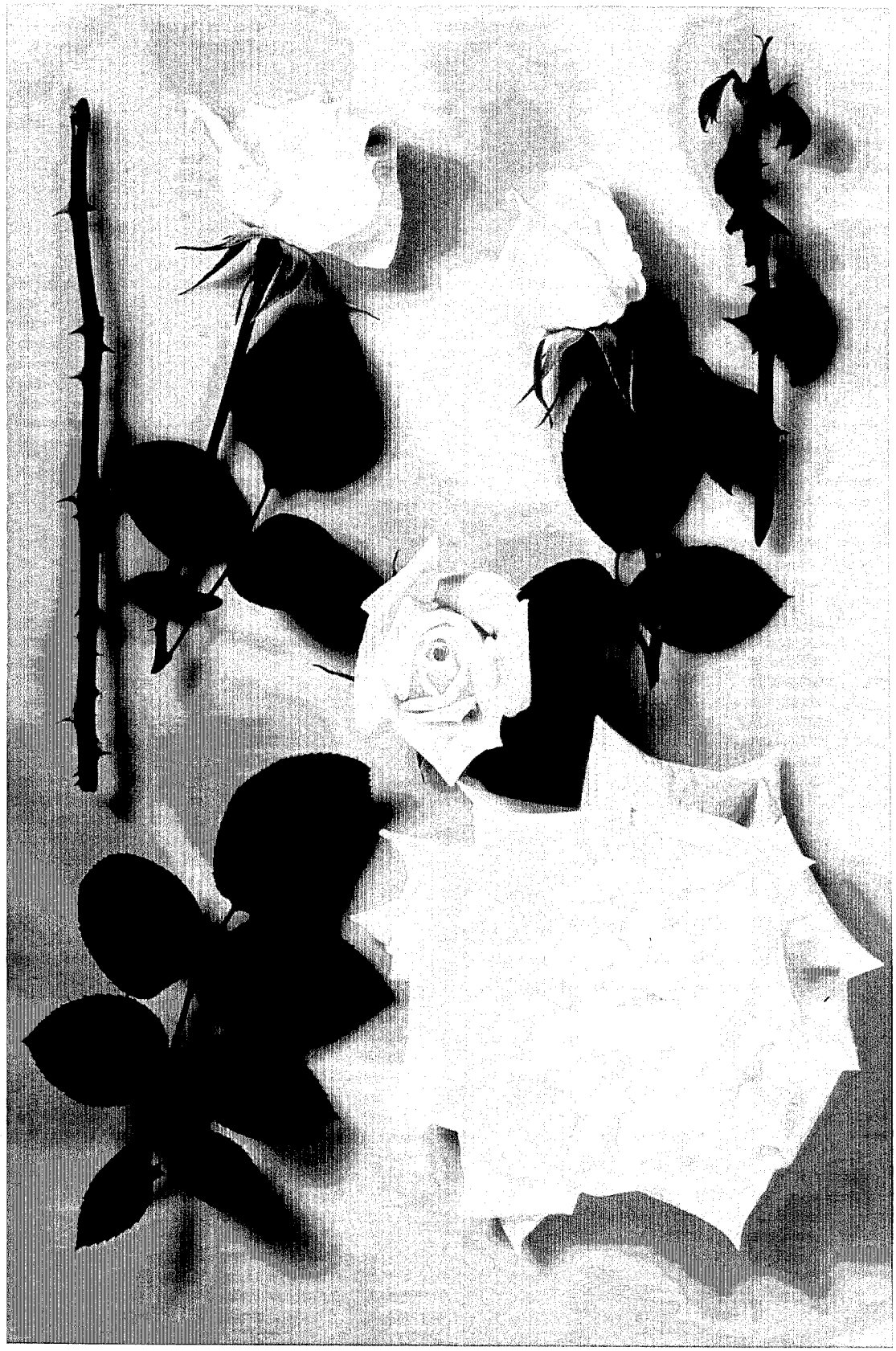

* * * * *